United States Patent [19]

Frenkel et al.

[11] Patent Number: 4,473,548

[45] Date of Patent: Sep. 25, 1984

[54] METHOD OF IMMUNIZING CATS AGAINST SHEDDING OF TOXOPLASMA OOCYSTS

[75] Inventors: Jacob K. Frenkel, Overland Park, Kans.; Donald D. Smith, Independence, Mo.

[73] Assignee: The Kansas University Endowment Association, Lawrence, Kans.

[21] Appl. No.: 403,539

[22] Filed: Jul. 30, 1982

[51] Int. Cl.³ .................... A61K 39/002; A61K 35/00
[52] U.S. Cl. ...................................... 424/88; 424/93; 424/114
[58] Field of Search ................... 424/114, 88, 93, 180, 424/181, 89

[56] References Cited

PUBLICATIONS

Frenkel, J., Vet. Med., Aug. 1982, pp. 1188–1194.
Frenkel, J., et al., J. Parasitol., vol. 68, 1982.
Sheffield, H., et al., Am. J. Trop. Med. Hygiene, vol. 25, pp. 379–383, 1975.
Melton, M., et al., J. Parasitology, vol. 61, pp. 713–717, 1975.
Dubey, J., et al., J. Parasitology, vol. 56, pp. 447–456, 1970.
Overdulve, J., 3 Int. Congr. Parasitology, Proceedings, vol. 1, pp. 302–303, 1974.
Ferguson, D., et al., 3 Int. Congr. Parasitology, Proceedings, vol. 1, pp. 106–107, 1974.
Sheffield, H., et al., 3 Int. Congr. Parasitology, Proceedings, vol. 1, pp. 106–107.
Dubey, J., et al., Vet. Path., vol. 11, pp. 350–379, 1974.
Frenkel, J., et al., J. Parasitol., vol. 68, 1982.
Meryagami, T., et al., J. Antibiotics, vol. 34, pp. 218–223, 1981.
Smith II, C., et al., J. Parasitol., vol 67, pp. 511–516, 1981.
Wilson, J., Can. Vet. J., vol. 21, pp. 30–31, 1980.
Frenkel, J., et al., Science, vol. 164, pp. 432–433, 1969.

*Primary Examiner*—Blondel Hazel
*Attorney, Agent, or Firm*—Schmidt, Johnson, Hovey & Williams

[57] ABSTRACT

A method of immunizing cats against shedding of Toxoplasma oocysts is described wherein cats are given a primary Toxoplasma infection, preferably by feeding of tissue cysts, and are chemoprophylactically treated to suppress oocyst shedding as a result of the primary infection. thus, the treated cats are given immunity to oocyst shedding without the necessity of initial shedding. The treating agent is preferably monensin given with the cats' daily ration at a level of at least about 200 mg. monensin per kg. of cat food. Other useful treating agents include salinomycin or a combination of orally administered sulfadiazine and pyrimethamine.

7 Claims, No Drawings

METHOD OF IMMUNIZING CATS AGAINST SHEDDING OF TOXOPLASMA OOCYSTS

BACKGROUND OF THE INVENTION

1. Field of the Invention

The present invention is broadly concerned with a method of immunizing cats against shedding of Toxoplasma oocysts in their fecal elimination processes. More particularly, it is concerned with such a method in which immunization can be accomplished without the necessity of incurring initial oocyst shedding as has heretofore been thought to be essential.

2. Description of the Prior Art

Cats and people are biologically close enough for them to be able to suffer from some of the same diseases and parasites. Some of these ailments are well known—rabies, because it is so dramatic and terrible, and fleas, because they are so common, are two familiar examples. Less familiar is Toxoplasmosis, an animal disease that can be transmitted to man. It is common to all domestic animals, including barnyard species, and, when present, is transmitted through cat feces and meat.

Any direct contact with cat feces increases the likelihood of contagion. Cattle and sheep can become infected by ingesting contaminated soil while grazing. Birds may become infected when eating seeds on the ground or from eating contaminated earthworms. However, a domestic cat, after stalking a mouse or bird, may disseminate the disease. Although all these infected animals may be means of transmitting disease, more often than not there is no sign of illness.

Toxoplasmosis is a parasitic disease, and research has indicated that the parasite has a complicated life cycle which spreads the disease through many animals. Oocysts (egg spores) are shed in the feces of domestic cats and certain types of wild cats. Oocysts are then spread by contact with the feces. Flies and cockroaches, which eat feces, can serve as transport agents, contaminating animals which do not directly encounter the cat feces. Mice and birds can be infected either from transport agents or through direct contact and can then spread the infection to animals which prey on them. Humans can be infected by eating raw or rare meats, or by direct contact with infected cat feces.

Toxoplasma infections are quite prevalent, with one-quarter to one-half of the adults in the United States and elsewhere asymptomatically infected. While the presence of Toxoplasma infections has long been known, little was discovered about the transmission of Toxoplasma until the late 1930's and 1940's when Toxoplasma was found in newborn babies in the U.S. However, the life cycle of Toxoplasma, and the central role played therein by cats, has now been conclusively established.

The spectrum of human disease due to Toxoplasma was characterized by a combination of serologic, immunologic and epidemiological studies, and by isolation of Toxoplasma. In the acute infection where cells are destroyed by rapidly proliferating organisms, there may occur fever, pneumonia, an inflammation of the heart muscle, liver and skin (rash). Toward the end of this period or following a subclinical acute infection, localized or generalized swelling of lymph nodes is observed, especially in women. In newborns infected in utero, a subacute disease picture is typical. In addition to the symptoms of acute Toxoplasmosis mentioned above, meningoencephalitis ("Brain fever"), often with hydrocephalus ("water on the brain"), and retinochoroiditis (intraocular inflammation) are important. Most of the mothers who have given birth to infected babies had infections without symptoms.

Thus, Toxoplasmosis deserves special attention because of the serious danger it raises for the unborn human baby. A pregnant woman may have the infection and unknowingly infect the fetus. If not diagnosed and treated in time, her child may be born with permanent brain and eye damage. For this reason, efforts to prevent infection during pregnancy are important.

Inasmuch as domestic cats are an important carrier of Toxoplasma and shed infectious oocysts in their feces, attempts have been made in the past to immunize such cats against oocyst shedding. Generally speaking, prior successful immunizations have required primary infection of cats with Toxoplasma, followed by the usual oocyst shedding and a buildup of immunity. However, this manner of immunization generates the very phenomenon sought to be avoided, i.e., oocyst shedding, and as such is deemed deficient. This is especially the case when it is considered that infectious oocysts tend to remain active for a period of months up to a year and a half.

Therefore, there is a decided need in the art for an effective method of immunizing cats against oocyst shedding without incurring oocyst shedding as a result of vaccination.

SUMMARY OF THE INVENTION

The present invention overcomes the problems noted and provides a greatly improved method of immunizing cats against shedding of Toxoplasma oocysts and such is accomplished without initial shedding which has characterized prior immunization attempts. Broadly speaking, the method of the invention involves initially infecting a cat by administration of Toxoplasma microorganisms such that the cat will, absent additional treatment, begin shedding Toxoplasma oocysts. Preferably, the administration is oral using Toxoplasma tissue cysts. Prior to the onset of such shedding, the cat is treated to suppress or prevent oocyst shedding. This treatment comprises the steps of orally administering to the cat an effective amount of a treating agent selected from the group consisting of monensin, salinomycin, and a combination of sulfadiazine and pyrimethamine. Oral administration of the treating agent is continued for a period of time in order to prevent or at least substantially minimize oocyst shedding as a result of the initial infection. The treatment should be of sufficient duration so that the treated cat is immunized against oocyst shedding in the event of subsequent Toxoplasma infection.

The most preferred treating agent is monensin, which is advantageously administered with the daily ration of the cat at a level of at least 200 mg. per kg. of cat ration. Most preferably this administration is about 200 to 300 mg. per kg. of cat ration. The preferred drug, monensin, is a biologically active compound produced by a fermentation process and is identified as 2-[5-Ethyltetrahydro-5-[tetrahydro-3-methyl-5-[tetrahydro-6-hydroxy-6-(hydroxymethyl)-3, 5-dimethyl-2Hpyran-2-yl]-2-furyl]-2-furyl]-9-hydroxy-$\beta$-methoxy-$\alpha$, $\gamma$,2,8-tetramethyl-1,6-dioxaspiro[4.5]decane-7-butyric acid. Salinomycin is characterized in a paper entitled "The Site of Action of the Anticoccidial Salinomycin (coxistac), *J. Parisitol.*, Vol. 65, p. 137 (1979), and this paper is incorporated by reference herein.

In the case of salinomycin, it is advisable to feed this agent with the daily ration of the cat at a level of at least about 50 mg. per kg. of cat ration, and more preferably at a level of 50 to 100 mg. per kg. of cat ration. Another preferred treating agent comprises a combination of sulfadiazine and pyrimethamine. Administration of this agent preferably involves feeding the sulfadiazine with the daily ration of the cat at a level of at least about 60 mg. per kg. of cat weight, whereas the pyrimethamine is orally administered in the form of a gelatin capsule at a level of at least about 1.0 mg. per kg. of cat weight. More preferably the sulfadiazine should be administered at a level of about 60 to 100 mg. per kg. of cat weight whereas the pyrimethamine should be given at a level of about 1 to 2 mg. per kg. of cat weight.

In general, treatment with the chemical treating agents should be commenced within about two days from the day of initial infection, and should continue for a period of at least about two weeks thereafter, usually on a daily basis. However, other administration schedules could be employed, so long as the aims of the invention are met.

DESCRIPTION OF THE PREFERRED EMBODIMENTS

The following example sets forth particularly preferred methods of the embodiments of the invention. It should be understood, however, that the example is given by way of illustration only and should not be taken in a limiting sense.

EXAMPLE

Materials and Methods

Toxoplasma

The M-7741 strain of Toxoplasma originally isolated from sheep in the United States, was used in this example.

Animals

Mice used to maintain the cyst stage of Toxoplasma were from the CF-1 line, obtained from Mid-Continent Research, Inc., Shawnee, Kans. 66203. Newly weaned kittens between 1.5 and 4 months of age weighing 440 to 2480 gm were utilized for most experiments. These kittens were raised in an animal facility or obtained as weanlings from private donors. Kittens were weighed, measured and bled from an ear vein prior to initial exposure to Toxoplasma, prior to each successive exposure and 30 to 40 days after the last exposure. Feces were collected prior to experimentation, and daily or at least three times weekly thereafter until termation of the experiment.

Fecal examination

Oocysts of Toxoplasma were separated from fecal material and concentrated by means of flotation in a sucrose solution of 1.15 Sp. Gr. (Frenkel, J. K., "Toxoplasmosis", In Current Veterinary Therapy, R. W. Kirk (ed.), W. B. Saunders Co., Philadelphia, 5: 775–780; 6; 1318–1324 (1974)). Their presence or absence was determined microscopically by scanning across a 22 mm coverslip, using both 100 and 400× magnifications. Samples were stored in 2% (v/v) sulfuric acid. A number of negative and positive specimens were inoculated as 10-fold dilutions into mice to check by seroconversion on the sensitivity of microscopic evaluations. A negative visual examination was usually negative in the mice, although quantitative relationships between the inoculum of cats and mice suggest that 10 and rarely under 100 oocysts per daily specimens could be overlooked. High total daily production varied between 100 thousand and 10 million oocysts.

Histologic examination

The small intestine of kittens to be examined was divided into five segments (Dubey, J. P. and Frenkel, J. K., "Cyst-induced Toxoplasmosis in Cats", J. Protozool., 19(1): 155–177, (1972)) which were flushed with Zenker-formol fixative, after which each segment was cut into 14 to 20 sections less than 10 mm in length and immersed in the fixative. Tissues were embedded in paraffin and stained with hematoxylin and eosin.

Serologic examination

Sera from cats and mice were examined for antibody in the Sabin-Feldman dye test using tachyzoites of the RH strain of Toxoplasma as antigen (Frenkel, J. K. and Jacobs, L., "Ocular Toxoplasmosis", A.M.A. Arch. Ophth., Chicago, 59: 260–279 (1958)), and citrated human serum as complement source (Schreiber, R. D. and Feldman, H. A., "Identification of the Activator System for Antibody to Toxoplasma as the Classical Complement Pathway", J. Infect. Dis., 141(3): 366-369 (1980)); (Wallace, G. D., "Sabin-Feldman Dye Test for Toxoplasmosis. The Use of Sodium Citrate in Accessory Factor, and a Method for Collecting and Storing Blood on Paper Discs", Am. J. Trop. Med. Hyg., 18: 395–398, (1969)). Titers are listed as the reciprocals of the serum dilution.

Infectious inocula and vaccines

All test kittens were initially infected by oral administration using live inocula bradyzoites (cysts from mouse brains). The Toxoplasma was administered orally. Doses for primary infection were 0.25–2.0 chronically infected mice.

Chemoprophylaxis

Infection together with prophylactic chemotherapy was employed. Crystalline monensin sodium (lots×34933 and×31357; 89.9% purity) was obtained from Lilly Research Labs of Greenfield, Ind. 46140. The powdered monensin was mixed in ground Purina Cat Chow as 200 mg/kg (20 mg. per 100 g). Sulfadiazine was given 60 mg. per kg. cat/day mixed with food, combined with pyrimethamine (Daraprim, Burroughs Wellcome), 1.0 mg/kg of cat weight, orally administered daily in a gelatin capsule. Control kittens were given powdered Purina Chow. These kittens were infected and reinfected with M-7741 bradyzoites.

Experimental design

A group of nine initially infected kittens were treated with monensin as indicated above, i.e., by mixing the monensin with the kitten ration. Monensin treatment was begun 1–2 days before primary infection, and was continued for a period of 8 to 21 days thereafter. Another group of four initially infected kittens were fed a combination of sulfadiazine and pyrimethamine, at the levels indicated above for a period of 21 days, commencing 1–2 days before infection.

After the primary infection/chemoprophylaxis treatment outlined, all of the kittens were challenged with the homologous M-7741 Toxoplasma strain. Such occurred 30–60 days after the above treatment was terminated. Doses for challenge were the same as used for primary infection. Failure of the cats to shed oocysts after challenge was taken as indication of immunity, if control cats were shedding.

Results

All thirteen of the treated cats were free of oocyst shedding after the initial infection, whereas all 13 controls shed oocysts.

After challenge, 11 of 12 of the control cats, 7 of 9 of the monensin treated cats, and all of the sulfadiazine/pyrimethamine treated cats, were immune. The results of this test are set forth in the Table.

TABLE

Immunity in Kittens in Which Oocysts Shedding Had Been Suppressed by Chemoprophylaxis and in Controls

| Drugs | Primary Infection | | | Challenge | | |
|---|---|---|---|---|---|---|
| | Oocyst shedding | Antibody titer[1] | | Immune | Antibody titer* | |
| | | (range) | (geom. mean) | | (range) | (geom. mean) |
| Monensin | 0/9 | <2 to 64 | 9 | 7/9 | <4 to 64 | 6 |
| Sulfadiazine-Pyrimethamine | 0/4 | <2 to 8 | 2 | 4/4 | <8 to 64 | 32 |
| Controls | 13/13 | <2 to 256 | 26 | 11/12 | <2 to 256 | 21 |
| Challenge controls | | | | 0/3 | | |

[1]Titers expressed as the reciprocal of serum dilution.

Discussion

The above results demonstrate that Toxoplasma immunity in cats can be developed without any oocyst shedding whatsoever. This was particularly surprising in that other cats fed an oocyst-less strain of Toxoplasma where only 2 of 23 cats developed immunity.

The reasons for this difference are not fully understood. It is believed, however, that the treated cats supported some developmental stages in the gut which evoked a broader immunity than the oocyst-less strain in which enteroepithelial development is either truncated or absent.

Immunity in the absence of antibody was observed in several cats, especially those treated with monensin (2/7) and sulfadiazine (3/4). Immunity in the absence of antibody was also observed following oocyst shedding in one of the eleven controls in the present experiments and described previously (Dubey, J. P., and Frenkel, J. K., "Cyst-induced Toxoplasmosis in Cats", *J. Protozool.* 19(1): 155–177 (1972)).

I claim:

1. A method of immunizing a cat against shedding of Toxoplasma oocysts which comprises the steps of:
    initially infecting said cat by administering to the cat Toxoplasma microorganisms such that the cat will, absent additional treatment, begin shedding Toxoplasma oocysts;
    prior to the onset of said shedding, treating said cat to suppress or prevent said oocyst shedding, said treating comprising the steps of orally administering to said cat an effective amount of a treating agent selected from the group consisting of monensin and salinomycin; and
    continuing such oral administration for a period of time after the first agent administration for preventing or substantially minimizing oocyst shedding as a result of said infection, and for permitting immunization to develop in said cat against oocyst shedding in the event of subsequent Toxoplasma infection.

2. The method as set forth in claim 1, said agent being monensin administered with the daily ration of said cat at a level of at least about 200 mg. per kg. of cat ration.

3. The method as set forth in claim 2, said level being from about 200 to 300 mg. per kg. of cat ration.

4. The method as set forth in claim 1, said agent being salinomycin fed with the daily ration of said cat at a level of at least 50 mg. per kg. of said ration.

5. The method as set forth in claim 4, said level being about 50 to 100 mg. per kg. of cat ration.

6. The method as set forth in claim 1, said administration of treating agent commencing within about two days from the day of said initial infection, and continuing for a period of at least about two weeks thereafter on a daily basis.

7. The method as set forth in claim 1, said administration being orally, said microorganisms being tissue cysts.

* * * * *